US008136415B2

(12) United States Patent
Tanaka

(10) Patent No.: US 8,136,415 B2
(45) Date of Patent: Mar. 20, 2012

(54) TRACTION APPARATUS AND TRACTION FORCE CONTROL METHOD FOR TRACTION APPARATUS

(75) Inventor: Noboru Tanaka, Kounosu (JP)

(73) Assignee: Ito Co., Ltd., Tokyo (JP)

( * ) Notice: Subject to any disclaimer, the term of this patent is extended or adjusted under 35 U.S.C. 154(b) by 392 days.

(21) Appl. No.: 12/516,513

(22) PCT Filed: Oct. 10, 2007

(86) PCT No.: PCT/JP2007/069754
§ 371 (c)(1),
(2), (4) Date: May 27, 2009

(87) PCT Pub. No.: WO2008/065810
PCT Pub. Date: Jun. 5, 2008

(65) Prior Publication Data
US 2010/0069810 A1    Mar. 18, 2010

(30) Foreign Application Priority Data

Dec. 1, 2006  (JP) ................................. 2006-325802

(51) Int. Cl.
*G01L 1/26* (2006.01)

(52) U.S. Cl. ..................................... 73/862.393; 73/760

(58) Field of Classification Search ................... 73/760, 73/862.393
See application file for complete search history.

(56) References Cited

U.S. PATENT DOCUMENTS

| 4,056,944 | A | * | 11/1977 | Lamy ............................ 405/170 |
| 4,539,979 | A | * | 9/1985 | Bremer .......................... 602/32 |
| 6,039,737 | A | | 3/2000 | Dyer |
| 7,601,132 | B2 | * | 10/2009 | Nichols et al. .................. 602/32 |
| 7,857,780 | B2 | * | 12/2010 | Sommers et al. ............... 602/36 |

(Continued)

FOREIGN PATENT DOCUMENTS

JP    56-018868    2/1981

(Continued)

OTHER PUBLICATIONS

Japanese Office Action issued on Aug. 11, 2009, for corresponding Japanese Patent Application 2006-325802.

*Primary Examiner* — Max Noori
(74) *Attorney, Agent, or Firm* — K&L Gates LLP

(57) ABSTRACT

A traction force control method for a traction apparatus according to the present invention that impresses a desired traction force on an object to be hauled via a traction mechanism is provided. The method includes measuring, in a zero traction state in which an impressed traction force that is impressed on the object to be hauled is zero, the impressed traction force with a traction force sensor and outputting a zero traction value. The method also includes generating an added value in which an adjusting output from a control circuit is added to the zero traction force value; providing the added value to a drive circuit of a drive mechanism that drives the traction mechanism and outputting a drive signal that corresponds to the added value; performing adjustment by increasing or decreasing the adjusting output so that the drive signal becomes a reference value that puts the object to be hauled in the zero traction state, setting the zero traction value as a zero point of the zero traction force sensor, and the adjusting output obtained by the adjustment step as a zero point of the control output of the control circuit, respectively.

7 Claims, 7 Drawing Sheets

U.S. PATENT DOCUMENTS

| | | | |
|---|---|---|---|
| 2005/0027226 A1* | 2/2005 | Stutz et al. | 602/32 |
| 2006/0108956 A1 | 5/2006 | Clark et al. | |
| 2009/0264804 A1* | 10/2009 | Tanaka | 602/32 |

FOREIGN PATENT DOCUMENTS

| | | |
|---|---|---|
| JP | 59-118156 | 7/1984 |
| JP | 7-13312 | 3/1995 |
| JP | 2002-522164 | 7/2002 |
| JP | 2003-088540 | 3/2003 |
| JP | 2004-348699 | 12/2004 |
| JP | 2004-359008 | 12/2004 |
| JP | 2006-166693 | 6/2006 |

* cited by examiner

TRACTION APPARATUS AND TRACTION FORCE CONTROL METHOD FOR TRACTION APPARATUS

CROSS REFERENCE TO RELATED APPLICATIONS

The present application is a National Stage of International Application No. PCT/JP2007/069754 filed on Oct. 10, 2007 and which claims priority to Japanese Patent Application No. 2006-325802 filed on Dec. 1, 2006, the entire contents of which are being incorporated herein by reference.

BACKGROUND

The present application relates to a traction apparatus that is used for traction performed in osteopathy, orthopedics, or the like and a traction force control method for the traction apparatus.

As for a conventional traction apparatus of this type, there has been proposed a sitting traction apparatus that is provided with a sling device for slinging up the underarms of a patient and a seat position that has a fixture for fixing the thighs, and so by hoisting the seat portion (upper half of the patient's body) vertically, treats the lumbar and the like (for example, refer to Japanese Unexamined Patent Application, First Publication No. 2003-88540).

Also as a conventional traction apparatus, there has been proposed a traction apparatus that has a load cell that detects traction force, and along with detecting traction force, is constituted so as to use the detection signal for drive control of a motor that is a drive source of traction force (for example, refer to Japanese Unexamined Patent Application, First Publication No. S59-118156).

A conventional traction apparatus displays the traction force on a display portion based on the detection output of a load cell serving as a traction force sensor during traction force control. This display uses an analog/digital conversion value (A/D value) of the output of the load cell, and a digital/analog conversion value (D/A value) that is a control signal corresponding to the traction force that has been set. This A/D signal and D/A signal use corrected values.

However, there are cases of the zero point of the output of the load cell that is a traction force sensor fluctuating due to a transitional state immediately after electrical power activation, an environmental change, or changes over time. Fluctuation of the zero point of a traction sensor directly influences the detection value of the traction force. Due to this influence, there has been the problem of not being able to accurately carry out traction force control.

As such, there is a need to provide a traction apparatus that is capable of accurately performing traction force control and a traction force control method for the traction apparatus.

SUMMARY

In an embodiment, a traction force control method for a traction apparatus that impresses a desired traction force on an object to be hauled via a traction mechanism includes the steps of: measuring in a zero traction state, in which an impressed traction force that is impressed on the object to be hauled is zero, the impressed traction force with a traction force sensor and outputting a zero traction force value; generating an added value in which an adjusting output from a control circuit is added to the zero traction force value; providing the added value to a drive circuit of a drive mechanism that drives the traction mechanism and outputting a drive signal that corresponds to the added value; performing adjustment by increasing or decreasing the adjusting output so that the drive signal becomes a reference value that puts the object to be hauled in the zero traction force state; and setting the zero traction value as a zero point of the zero traction force sensor, and the adjusting output obtained by the adjustment step as a zero point of the control output of the control circuit, respectively.

The aforementioned drive signal may be a pulse width modulation signal, and in the adjustment step the pulse width modulation signal may be adjusted so as to become the reference value that is defined by a duty ratio of the pulse width modulation signal.

The aforementioned traction force control method may be performed prior to impressing the desired traction force on the object to be hauled.

The aforementioned traction force control method may be performed when stopping the impression of the desired traction force on the object to be hauled.

In the traction force control method for a traction apparatus according to the embodiment with the aforementioned constitution, the output of the traction force sensor that detects the traction force that is impressed on an object to be hauled performs zero point adjustment of the output of the traction force sensor and the control output of the control circuit when the traction force impressed on the object to be hauled is zero.

Also, a traction apparatus according to the embodiment that impresses a desired traction force on an object to be hauled includes: a control portion that sets a traction force to be impressed on the object to be hauled; a traction mechanism including a fixture that is attached to the object to be hauled and a wire that is coupled to the fixture and impressing the traction force on the object to be hauled; a drive mechanism that winds up the wire; a drive circuit that supplies a drive signal to the drive mechanism; a traction force sensor that detects the traction force impressed on the wire; and a control circuit that supplies a control signal for performing drive control of the drive mechanism to the drive circuit based on a set output of a set traction force set by the control portion and a detection output of the traction force sensor, the control circuit adjusting the drive signal by outputting a signal that corrects an output of the traction force sensor so that the drive signal becomes a reference value that causes the drive mechanism to generate no drive force when a traction force impressed on the object to be hauled is zero, and the set traction force is not set by the control portion.

The control circuit may adjust the drive signal so as to become the reference value prior to impressing the desired traction force on the object to be hauled of the drive signal.

The control circuit may adjust the drive signal so as to become the reference value when stopping the impression of the desired traction force on the object to be hauled.

In the traction apparatus according to the embodiment with the aforementioned constitution, the control circuit makes the drive circuit stop the output of the drive signal to the motor as the drive mechanism. In the state of having stopped the driving of this motor, the control output of the control circuit corrects the output of the traction force sensor when the traction force that is impressed on the object to be hauled is zero, whereby the drive signal of the drive circuit is adjusted to the original value when the traction force is zero.

Accordingly, since zero point adjustment of the traction force sensor is performed in accordance with the traction force control method and the traction apparatus of the embodiment, it is possible to accurately control the traction force that is impressed on an object to be hauled corresponding to a set value even if the zero point of the traction force sensor fluctuates due to a transitional state immediately after electrical power activation, an environmental change, or changes over time, and so the accuracy of the traction force control can be enhanced.

As described above, since zero point adjustment of the traction force sensor and the control output of the control circuit is performed in accordance with the embodiment, it is possible to accurately control the traction force that is impressed on an object to be hauled corresponding to a set value even if the zero point of the traction force sensor fluctuates due to a transitional state immediately after electrical power activation, an environmental change, or changes over time, and so the accuracy of the traction force control can be enhanced.

Additional features and advantages are described herein, and will be apparent from, the following Detailed Description and the figures.

DETAILED DESCRIPTION

Figure 1:
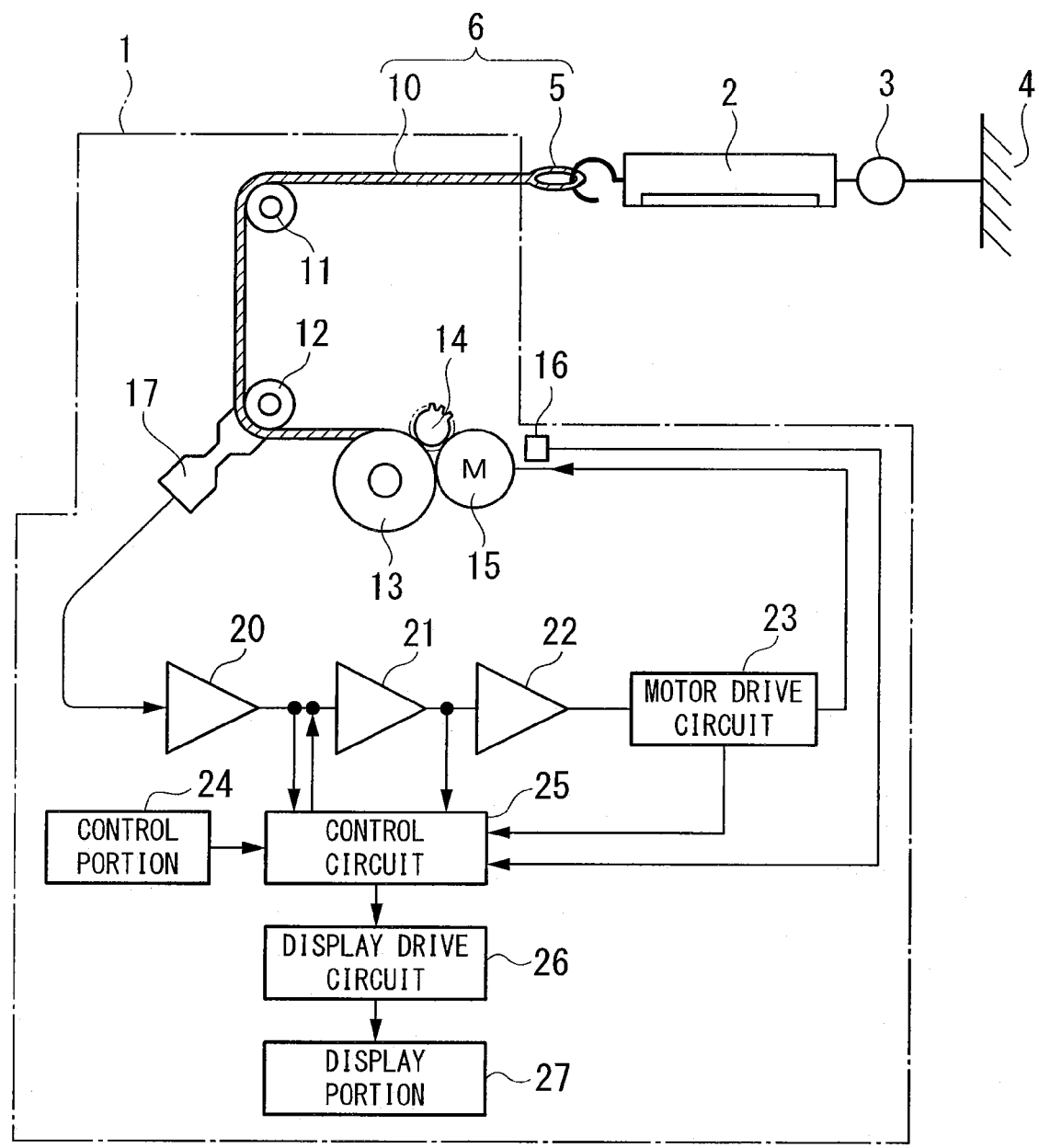
FIG. 1 is a diagram that shows an overall schematic configuration of a traction apparatus in accordance with an embodiment.

An embodiment shall be described in detail with reference to the drawings. FIG. 1 shows a schematic configuration of a traction apparatus in accordance with an embodiment. In FIG. 1, a traction apparatus 1 in accordance with the present embodiment is coupled to a fixing portion 4 by a wire 10 via a fixture 3 and an object to be hauled 2. The object to be hauled 2 is an elastic body, and although schematically illustrated in FIG. 1, is for example a human body.

The traction apparatus 1 has a control portion 24, a traction mechanism 6, a motor (drive mechanism) 15, a load cell (traction force sensor) 17, and a control circuit 25. The control portion 24 sets the traction force to be impressed on the object to be hauled 2. The traction mechanism 6 includes a fixture 5 that is attached to the object to be hauled 2 and the wire 10 that is coupled to the fixture 5. The traction mechanism 6 impresses traction force on the object to be hauled 2. The motor 15 winds up the wire 10. The load cell 17 detects the traction force that acts on the wire 10. The control circuit 25 takes in the set output of the traction force that is set by the control portion 24 and the detected output of the of the load cell 17, and performs drive control of the motor (drive mechanism) 15.

The wire 10 is taken up by a take-up roller 13 via pulleys 11 and 12. The drive force thereof is the rotative force of the motor 15, and is transmitted to the rotation shaft of the take-up roller 13 via a reduction mechanism 14.

A rotational number detector 16 is a detector that detects the number of times that the motor has rotated. The detection output of the rotation number detector 16 is input to a control circuit 25.

Also, the traction apparatus 1 includes a direct current amplifier 20, an adder 21, a pulse width modulation (PWM) converter 22, a motor drive circuit 23, a display portion 27, and a display drive circuit 26. The direct current amplifier 20 amplifies the detection output of the load cell 17. The adder 21 adds the output signal of the direct current amplifier 20 and the control signal that is outputted from the control circuit 25. The PWM converter 22 outputs the pulse signal of a duty according to the output level of the adder 21. The motor drive circuit 23 outputs a drive signal to the motor 15. The display drive circuit 26 drives the display portion 27.

The control circuit 25 performs the following traction force control processing. First, the control circuit 25, by means of a first traction force control, winds up the slack portion of the wire 10 by the motor 15 to eliminate the slack of the wire 10 that is coupled to the object to be hauled 2. Next, the control circuit 25, by means of a second traction force control, converts the set traction force that is set by the control portion 24 to a traction amount to calculate a conversion value, and with a predetermined amount of the traction amount that was set based on the conversion value serving as an initial target value, continuously winds up the wire 10 by the motor 15 until that initial target amount. Next, the control circuit 25, by means of a third traction force control, detects the traction force being impressed on the object to be hauled 2 by the load cell 17, and by making the set traction force a final target value based on the detection output of the load cell 17, along with computing the drive stoppage time of the motor 15, drives the drive mechanism and stops the driving of the motor 15 at the point of reaching that drive stoppage time.

The control portion 24 is constituted by a plurality of keys. The display portion 27 displays the functions of the keys of the control portion 24, the medical treatment mode, various parameters, the traction force, errors, and the like.

Figure 2:
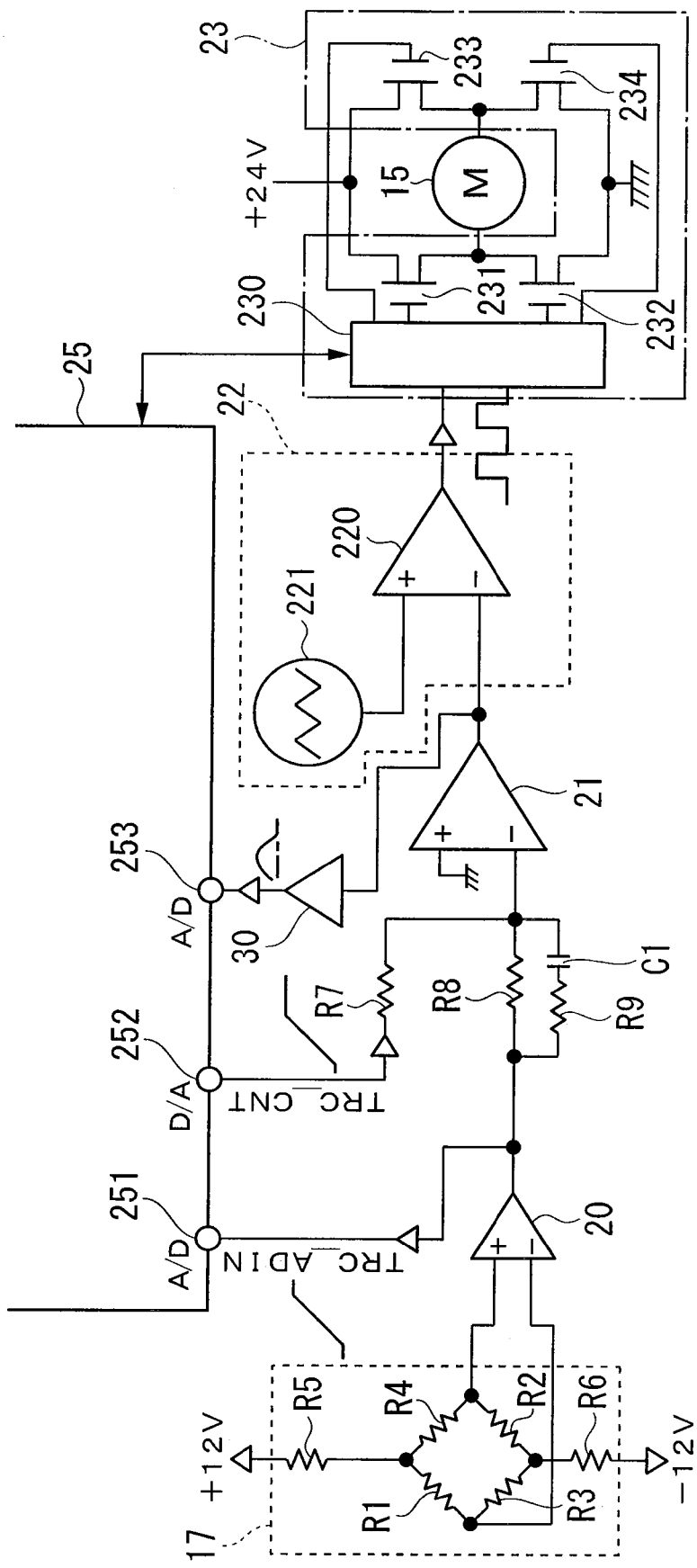
FIG. 2 is a circuit diagram that shows a specific constitution in essential portions of the traction apparatus in accordance with the embodiment shown in FIG. 1.

Next, a specific configuration relating to traction force control for the traction apparatus shown in FIG. 1 is shown in FIG. 2. In FIG. 2, elements that are identical to those illustrated in FIG. 1 are denoted by the same reference symbols, and overlapping descriptions are omitted.

In FIG. 2, the load cell 17 has a bridge circuit which is composed by resistors R1, R2, R3, and R4, and resistors R5 and R6. A power supply voltage is impressed on the bridge circuit via the resistors R5 and R6. When a traction force acts on the wire 10, the balance of the bridge circuit is disturbed, and a direct current voltage of a level corresponding to the magnitude of the traction force is output.

The direct current amplifier 20 inputs a signal TRC_ADIN, which is generated by amplifying the output of the bridge circuit, that is, the detection output of the load cell 17, into a terminal 251 of the control circuit 25. Hereinbelow, the output after amplifying the output of the load cell 17 by the direct current amplifier 20 shall be called the output of the load cell 17.

A control output TRC_CNT corresponding to the traction force set by the control portion 24 from a terminal 252 of the control circuit 25 and the signal TRC_ADIN are added in the adder 21. The addition output is inputted to a terminal 253 of the control circuit 25, and input to an inverting input terminal of a comparator 220 that constitutes the PWM converter 22.

On the other hand, a triangular wave signal outputted from a triangular wave generator 221 is input to a non-inverting input terminal of the comparator 220. This triangular wave signal and the output of the adder 21 are compared by the comparator 220, whereby a pulse signal with a duty corresponding to the output level of the adder 21 is output to the motor drive circuit 23.

In the motor drive circuit 23, a voltage of for example +24 V is impressed across both terminals of the motor 15 via switching elements 231 and 233. Both terminals of the motor 15 are grounded via switching elements 232 and 234. Based on the control signal that is output from the control circuit 25, the switching elements 231 to 234 are turning ON and OFF controlled so that the motor 15 rotates in the forward direction or reverse direction. That is, the control signal from the control circuit 25 is input to the motor drive circuit 23, and the output signal of the comparator 220 is output to the gate of a specified switching element among the switching elements 231 to 234.

Figure 3:
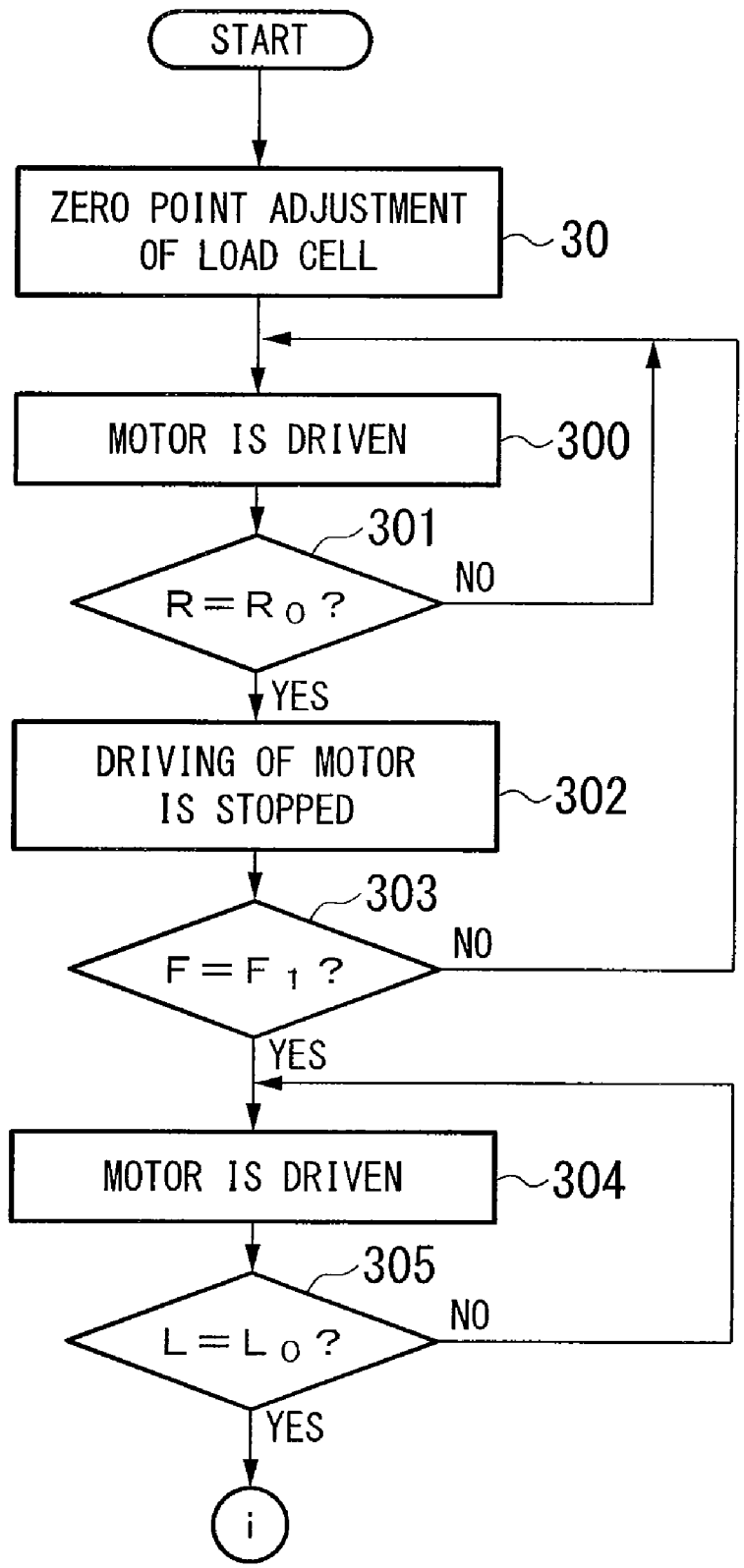
FIG. 3 is a flowchart that shows the operation of the traction apparatus in accordance with the embodiment shown in FIG. 1.
Figure 4:
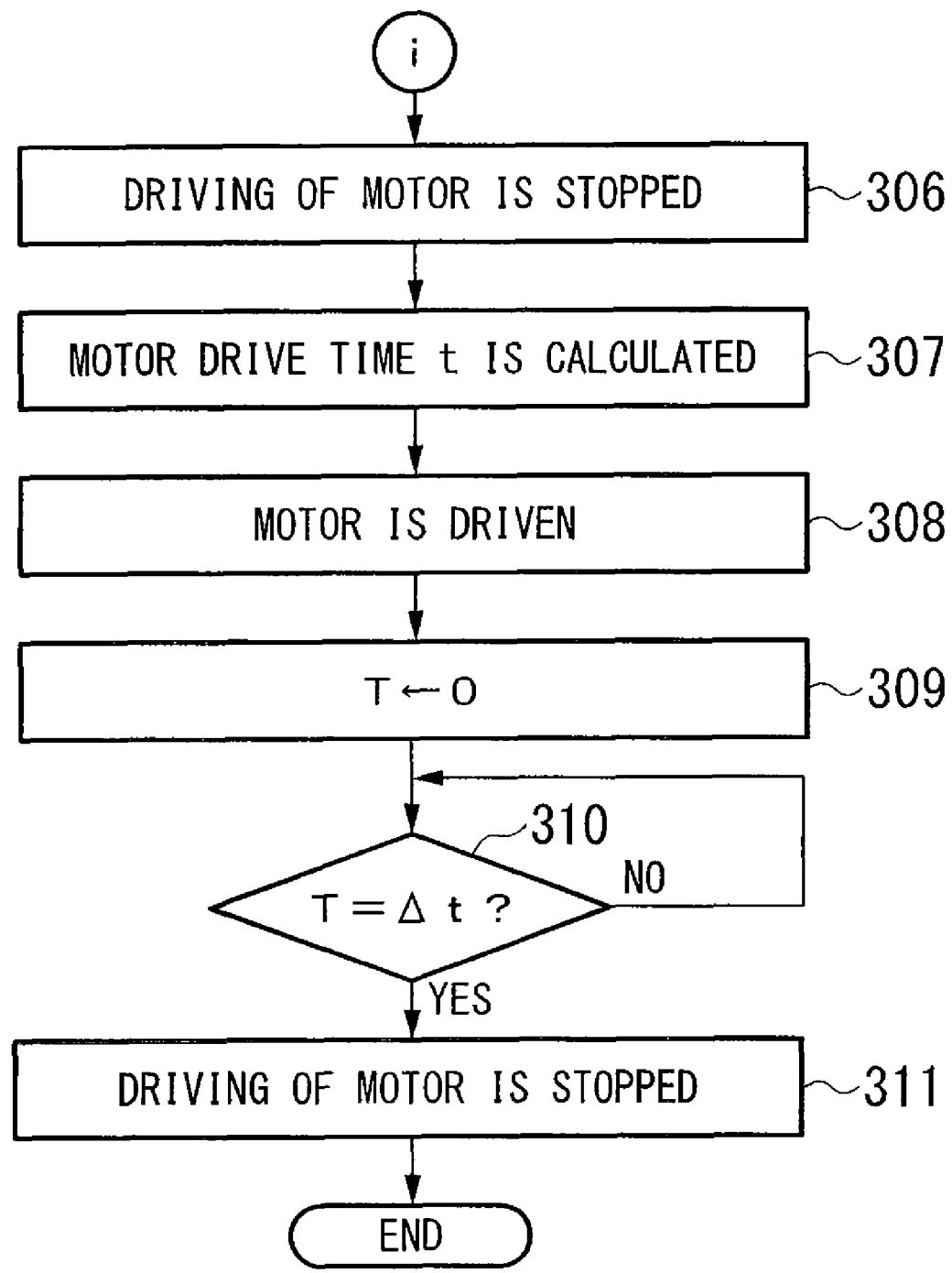
FIG. 4 is a flowchart that shows the operation of the traction apparatus in accordance with the embodiment shown in FIG. 1.
Figure 5:
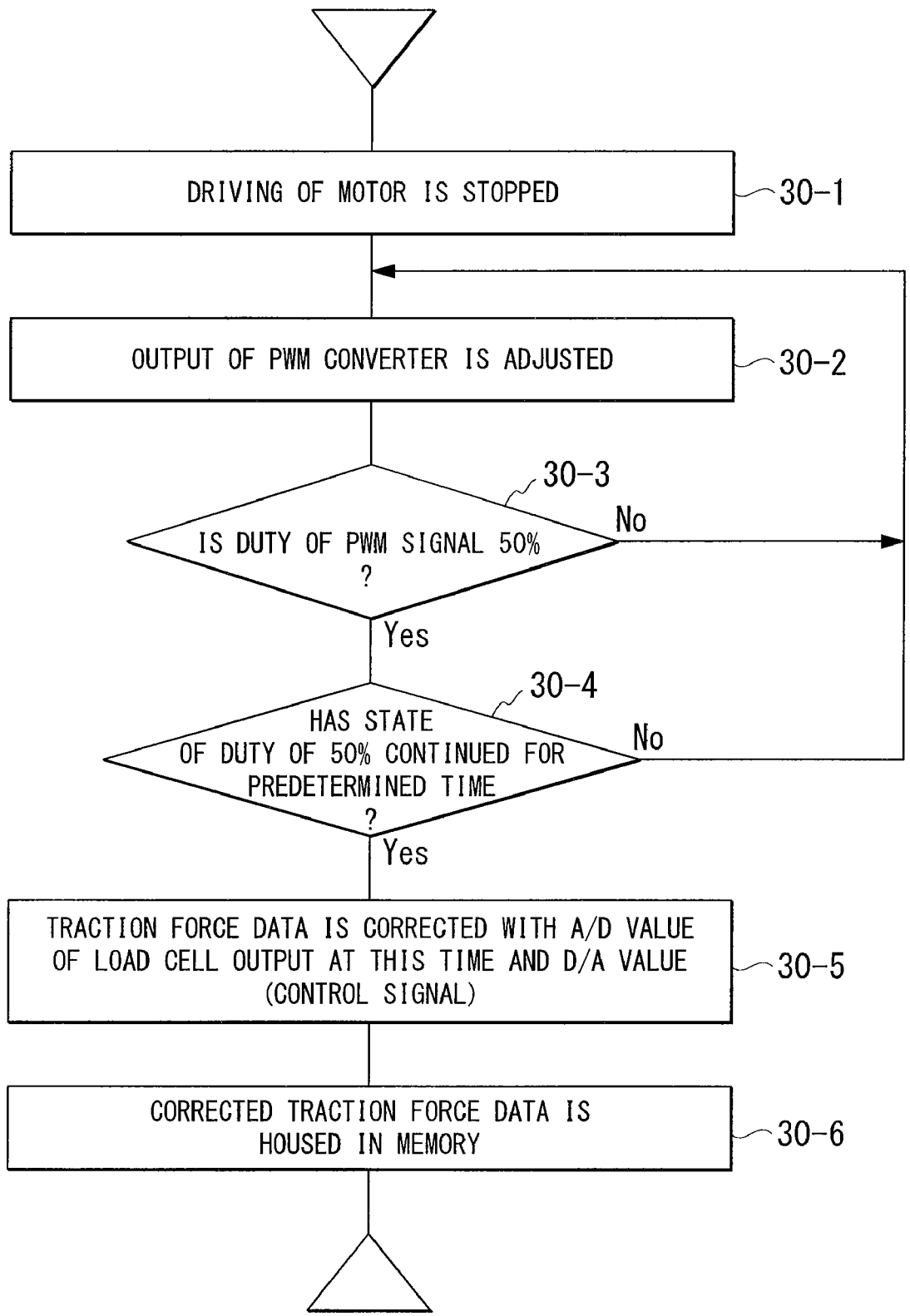
FIG. 5 is a flowchart that shows the processing content during zero point adjustment of a load cell in accordance with the embodiment shown in FIG. 1.

The operation of the traction apparatus of the abovementioned constitution shall be described with reference to the flowcharts of FIG. 3 to FIG. 5. In these drawings, zero point adjustment of the load cell 17 serving as a traction force sensor is performed at the start of traction force control (Step 30). Here, referring to FIG. 5, the process content of this Step 30 shall be described in detail. In Step 30-1, the control circuit 25 outputs a control signal to the motor drive circuit 23 so as to stop the output of the drive signal (the output signal of the comparator 220) from the motor drive circuit 23 to the motor 15. As a result, the rotational driving of the motor 15 is stopped. At this time, the output value of the load cell when this traction force is not impressed is stored in the memory in the control circuit. In this state, traction force is not impressed on the object to be hauled 2. Accordingly, in the normal situation, the output value at this time of the load cell 17 that functions as a traction force sensor should be a value that is equivalent to zero (kg) if the zero point has not fluctuated due to changes over time or the like. If the output of the load cell 17 is a value that is equivalent to zero, in the state of not adding the adjusting output from the terminal 252 of the control circuit 25, the duty of the PWM signal that is output from the PWM converter 22 is 50% (reference value). When the duty of the PWM signal is 50%, the motor 15 is set so as not to be driven. Also, during the processing of this Step 30, the PWM signal is input to a motor driver 230 that constitutes the motor drive circuit 23. However, during processing of the Step 30, since the output from the motor driver 230 to the motor 15 is turned OFF, the motor 15 is not driven.

Figure 6:
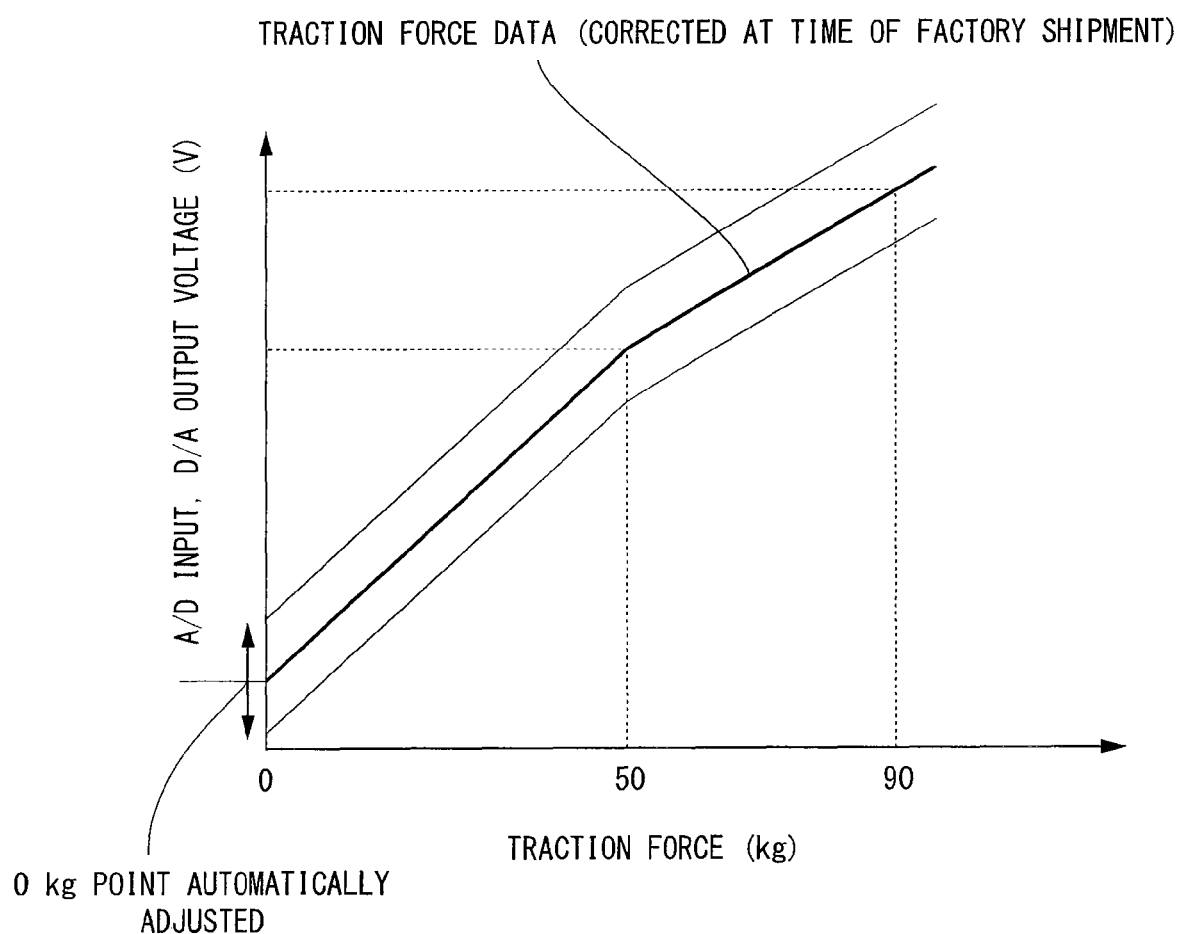
FIG. 6 is a descriptive view that shows the state during zero point adjustment of the load cell in accordance with the embodiment shown in FIG. 1.

Here, FIG. 6 shows the traction force data (the data already corrected when shipped from the factory) that shows the relation between the A/D value of the output of the load cell 17 (TRC_ADIN) and the traction force. In the traction force data of FIG. 6, the vertical axis shows the A/D value of the output of the load cell 17. The zero point of the A/D value of the output of the load cell 17 of this traction force data is corrected. That is, the zero point of this A/D value is corrected to the output value of the load cell 17 that is stored in the above-mentioned memory and acquired when the traction force is not impressed. For example, suppose that the A/D value of the output of the load cell 17 when a traction force is not impressed is 1 V. In this case, zero point correction is performed that sets the zero point when the traction force on this vertical axis is 0 kg as 1 V. From the relation of the traction force and the A/D input with this corrected zero point serving as a reference, the control circuit 25 computes the traction force that is loaded on the object to be hauled based on the A/D value of the output of the load cell 17 during traction force control.

Next, output adjustment of the PWM converter 22 is performed (Step 30-2). That is, the duty of the PWM signal that is the output signal of the PWM converter 22 is adjusted. The duty of this PWM signal is performed by increasing or decreasing the level of the control output TRC_CNT outputted from the terminal 252 of the control circuit 25. When the duty of the PWM signal is less than 50%, the level of this control output TRC_CNT is adjusted so as to be made to increase, and when the duty of the PWM signal exceeds 50%, the level of this control output TRC_CNT is adjusted so as to be made to decrease.

Next, as a result of increasing or decreasing the level of the control output TRC_CNT outputted from the terminal 252 of the PWM signal control circuit 25, it is judged whether or not the duty of the PWM signal which is an output signal of the PWM converter 22 has become 50% (Step 30-3). When the duty of the PWM signal is not 50%, the processing returns to Step 30-2, and the same process is repeated.

The PWM signal inputted from the PWM converter 22 to the motor driver 230 is further inputted from the motor driver 230 to the control circuit 25. Using the signal that has been input to this control circuit 25, judgment of the duty of the PWM signal is performed in the control circuit 25.

When the duty of the PWM signal becomes 50% in Step 30-3, processing proceeds to Step 30-4. Next, at Step 30-4, it is judged whether or not the state in which the duty of the PWM signal becoming 50% has continued for a predetermined time (for example, 2 seconds). In the case of the judgment being NO, the processing returns to Step 30-2, and the same processing mentioned already is repeated.

On the other hand, in the case of the state in which the duty of the PWM signal becoming 50% is judged as having continued for a predetermined time in Step 30-4, the adjustment of the zero point (0 kg point) is judged as having been completed. Here, FIG. 6 is also traction force data that shows the relation between the control output TRC_CNT and the traction force. In the traction force data of FIG. 6, the vertical axis also shows the D/A value of the control output. In the traction force data of FIG. 6, the zero point of the D/A value (TRC_CNT) that is a control signal that shows the magnitude corresponding to the set value of the traction force that is output from the control circuit 25 is corrected (Step 30-5). That is, the D/A value of the control output when the state in which the duty of the PWM signal becoming 50% has been judged as having continued for a predetermined time in Step 30-4 is corrected as a value of the zero point of the control output D/A. For example, suppose that the control output D/A value when the duty of the PWM signal is corrected to 50% is p V. In this case, zero point correction is performed that sets the zero point of the control output D/A when the traction force on the vertical axis is 0 kg as p V. From the relation between the traction force and control output TRC_CNT with this corrected zero point serving as a reference, the control circuit 25 computes the value of control output TRC_CNT corresponding to the set traction force to be impressed on the object to be hauled.

The aforementioned traction force data of the zero point value of the corrected control output D/A value is housed in the memory in the control circuit (Step 30-6), and this load cell zero point adjustment process is completed. As shown above, the zero point correction of the traction force data of FIG. 6 is separately performed with the output of the load cell 17 and the control output of a control circuit, respectively. The traction force data housed in this memory is subsequently used for the setting of the traction force by the control portion 24 and the traction force control. That is, this traction force data is used for computing the traction force that is loaded on the object to be hauled based on the A/D value of the output of the load cell 17. At this time, data is used in which the output value of the load cell when this traction force is not being impressed is corrected as the zero point. Moreover, this traction force data is used for computing the output value of the control output TRC_CNT from the traction force impressed on the object to be hauled. At this time, data is used in which the output value of the control output TRC_CNT when the state of the duty of the PWM signal becoming 50% is judged as having continued for a predetermined time is set as the zero point. In the following traction force control, the traction force being impressed on the object to be hauled from the output of the load cell 17 is computed using the traction force data corrected as mentioned above. Moreover, setting of the magnitude of the output signal of the control circuit according to the set traction force impressed on the object to be hauled is performed using this traction force data.

This step 30 can also be performed when the traction force control operation is stopped (when impressing of the desired traction force on the object to be hauled is stopped).

The description shall be given returning to FIG. 3 and FIG. 4. In FIG. 3 and FIG. 4, when the traction force that becomes the desired target value is set by the user using the control portion 24 and a switch for starting the traction operation is operated, the motor 15 is driven (Step 300). Next, it is judged whether or not the number of times R which the motor 15 has rotated based on the detection output of the rotational number detector 16 has become R=$R_0$ ($R_0$ is the number of times of rotations corresponding to the amount of traction at the time of initial traction.) (Step 301). In the case of the judgment of Step 301 being NO, the processing returns to Step 300, and rotational driving of the motor 15 is continued.

Also, when the judgment of Step 301 being YES, driving of the motor 15 is stopped (Step 302). Next, it is judged whether or not the traction force F has become F=$F_1$ (Step 303). That is, it is judged whether or not the traction force F that is impressed on the object to be hauled 2 has reached the traction force $F_1$ that is sufficient for taking up the slack portion of the wire 10. The judgment of this traction force $F_1$ uses the traction force that is calculated from the A/D value (TRC_ADIN) based on the output of the load cell 17 using the traction force data of FIG. 6. This traction force $F_1$ is set to for example 5 kg in the present embodiment. In the case of the judgment of Step 303 being NO, the process returns to Step 300. In this way, in order to take up the slack portion of the wire 10, the motor 15 is rotated a little, then stopped, and this operation is repeated until the rotation force F becomes F=$F_1$.

These Steps 300 to 303 constitute the first traction force control process.

Figure 7:
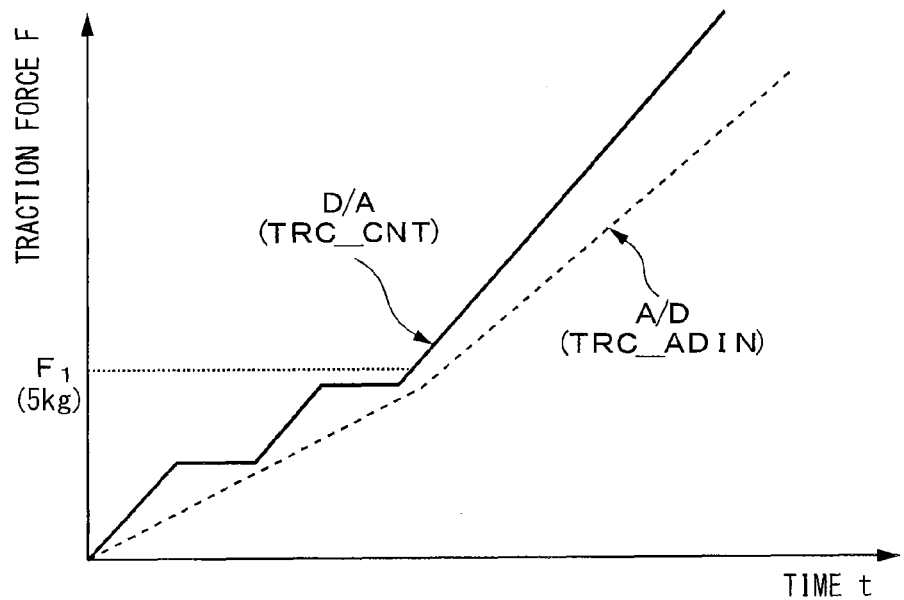
FIG. 7 is a view that shows an example of the control characteristics during the initial traction of a traction apparatus in accordance with another embodiment.

Here, in the aforementioned traction force control, rotating the motor a little, stopping it, and judging whether or not the predetermined traction force $F_1$ has been reached are repeatedly performed. As another method, as shown in FIG. 7, during the initial traction directly after the start of the traction force control, as for the traction until the traction force $F_1$ (5 kg) sufficient for taking up the slack portion of the wire 10, the following traction force control may be performed. First, the control output TRC_CNT is raised. Subsequently, when the control output TRC_CNT of the control circuit 25 is compared with output signal TRC_ADIN of the direct current amplifier 20 and there is a difference of 2 kg or more, the raising of the control output TRC_CNT of the control circuit 25 is stopped. Then, when the difference of this traction force has become 1 kg or less, the raising of the control output TRC_CNT is resumed. This traction force control is repeatedly performed until the traction force reaches $F_1$.

On the other hand, when the judgment of Step 303 is YES, the first traction force control process is completed and the processing proceeds to the second traction force control process that substantially causes the traction force to act on the object to be hauled 2.

That is, the driving of the motor is resumed (Step 304). Next, it is judged whether or not the traction amount L is L=$L_0$ ($L_0$ is assumed in the present embodiment for example to be 75% of the value of a traction amount obtained by converting a traction force $F_i$ that is the target value.) (Step 305). In this judgment, the traction amount is calculated based on the number of times of rotations detected by the rotational number detector 16. If the judgment of this Step 305 is NO, the processing returns to Step 304, and if YES, it proceeds to the next process step.

The schematic of the second traction force control process is as mentioned above, but in Step 305, the judgment may be made with the traction force instead of the traction amount. Hereinbelow, the specific operation of performing judgment with the traction force shall be described.

Figure 8:
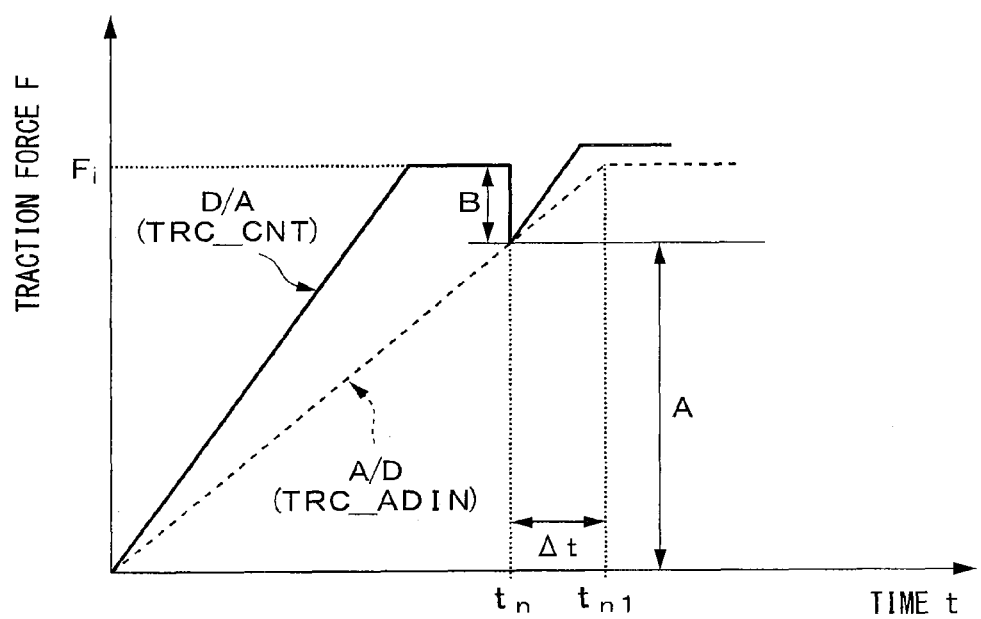
FIG. 8 is a view that shows an example of the traction force control characteristics of the traction apparatus in accordance with the embodiment shown in FIG. 1.

In the second traction force control process, as shown in FIG. 8, the control output TRC_CNT is raised at a set speed until the set traction force $F_i$. At this time, the magnitude of the control output TRC_CNT is computed based on the set traction force $F_i$ using the traction force data of FIG. 6. When the control output TRC_CNT reaches the set traction force $F_i$, that value is maintained. Next, if at time $t_n$ where the output signal TRC_ADIN of the direct current amplifier 20 which is converted to a traction amount reaches 75% of the set traction force $F_i$ (the point of A in FIG. 8), that is, the judgment of Step 305 is YES, the value of control output TRC_CNT is lowered to a level of 75% of the set traction force $F_i$ (an amount that is equivalent to B in FIG. 8).

The processing proceeds to the third traction force control process that raises the level of the control output TRC_CNT from this position at a set traction speed. In this third traction force control process, control is performed that stops the traction by the motor 15 in the state of the traction force that is impressed on the object to be hauled correctly conforming with the set traction force $F_1$ that is the target value.

In the third traction process, first, at time $t_n$, the driving of the motor 15 is stopped (Step 306). Next, a drive time Δt of the motor 15 that is required for the traction force that is impressed on the object to be hauled 2 to reach the set traction force $F_i$ is calculated based on the detection output of the load cell 17 (Step 307). Next, along with driving the motor 15, the timer T that times the drive time of the motor 15 is reset (Steps 308 and 309). Next, a judgment is made whether or not the drive time T of the motor 15 has reached T=Δt (Step 310). When the drive time T of the motor 15 has reached T=Δt time $t_{n1}$, the driving of the motor 15 is stopped (Step 311).

As described above, according to the traction apparatus in accordance with the present embodiment, since zero point adjustment of the traction force sensor is performed at the start of traction force control, it is possible to accurately control the traction force that is impressed on the object to be hauled corresponding to a set value even if the zero point of the traction force sensor fluctuates due to a transitional state immediately after electrical power activation, an environmental change, or changes over time, and so the accuracy of the traction force control can be enhanced.

The embodiment can be applied to a traction apparatus and a traction force control method that are used in osteopathy, orthopedics, or the like. According to this traction apparatus, since zero point adjustment of the traction force sensor is performed at the start of traction force control, it is possible to accurately control the traction force that is impressed on the object to be hauled corresponding to a set value even if the zero point of the traction force sensor fluctuates due to a transitional state immediately after electrical power activation, an environmental change, or changes over time, and so the accuracy of the traction force control can be enhanced.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention claimed is:

1. A method of traction force control for a traction apparatus that impresses a desired traction force on an object to be hauled via a traction mechanism, the method comprising:
    measuring, in a zero traction state in which an impressed traction force that is impressed on the object to be hauled is zero, the impressed traction force with a traction force sensor and outputting a zero traction value;
    generating an added value in which an adjusting output from a control circuit is added to the zero traction force value;
    providing the added value to a drive circuit of a drive mechanism that drives the traction mechanism and outputting a drive signal that corresponds to the added value;
    performing adjustment by increasing or decreasing the adjusting output so that the drive signal becomes a reference value that puts the object to be hauled in the zero traction state; and
    setting the zero traction value as a zero point of the zero traction force sensor, and the adjusting output obtained by the adjustment step as a zero point of the control output of the control circuit, respectively.

2. The method of traction force control according to claim 1, wherein the drive signal is a pulse width modulation signal, and in the adjustment step the pulse width modulation signal is adjusted so as to become the reference value that is defined by a duty ratio of the pulse width modulation signal.

3. The method of traction force control for a traction apparatus according to claim 1, wherein the traction force control method is performed prior to impressing the desired traction force on the object to be hauled.

4. The method of traction force control for a traction apparatus according to claim 1, wherein the traction force control method is performed when stopping the impression of the desired traction force on the object to be hauled.

5. A traction apparatus that impresses a desired traction force on an object to be hauled, the traction apparatus comprising:
    a control portion that sets a traction force to be impressed on the object to be hauled;
    a traction mechanism including a fixture that is attached to the object to be hauled and a wire that is coupled to the fixture and impressing the traction force on the object to be hauled;
    a drive mechanism that winds up the wire;
    a drive circuit that supplies a drive signal to the drive mechanism;
    a traction force sensor that detects the traction force impressed on the wire; and
    a control circuit that supplies a control signal for performing drive control of the drive mechanism to the drive circuit based on a set output of a set traction force set by the control portion and a detection output of the traction force sensor,
    the control circuit adjusting the drive signal by outputting a signal that corrects an output of the traction force sensor so that the drive signal becomes a reference value that causes the drive mechanism to generate no drive force when a traction force impressed on the object to be hauled is zero, and the set traction force is not set by the control portion.

6. The traction apparatus according to claim 5, wherein the control circuit adjusts the drive signal so as to become the reference value prior to impressing the desired traction force on the object to be hauled of the drive signal.

7. The traction apparatus according to claim 5, wherein the control circuit adjusts the drive signal so as to become the reference value when stopping the impression of the desired traction force on the object to be hauled.

* * * * *